(12) United States Patent
Cosse

(10) Patent No.: US 8,070,488 B2
(45) Date of Patent: *Dec. 6, 2011

(54) ORTHODONTIC TREATMENT METHODS, SYSTEMS AND APPARATUS FOR USE THEREWITH

(76) Inventor: Christopher C. Cosse, Shreveport, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/852,885

(22) Filed: Aug. 9, 2010

(65) Prior Publication Data

US 2010/0323317 A1    Dec. 23, 2010

Related U.S. Application Data

(63) Continuation of application No. 11/708,769, filed on Feb. 20, 2007, now Pat. No. 7,771,640.

(60) Provisional application No. 60/774,701, filed on Feb. 17, 2006.

(51) Int. Cl.
*A61C 3/00* (2006.01)
*B29C 59/00* (2006.01)
*D04H 1/00* (2006.01)
*B29C 67/00* (2006.01)

(52) U.S. Cl. ............................ 433/24; 264/222; 264/225

(58) Field of Classification Search ................ 433/8–16, 433/20–22, 24, 213–214; 264/222, 225, 264/16–20; 29/896.1, 896.11
See application file for complete search history.

(56) References Cited

U.S. PATENT DOCUMENTS

| | | | |
|---|---|---|---|
| 1,280,628 A | 10/1918 | Angle | |
| 1,821,171 A | 9/1931 | Atkinson | |
| 2,921,371 A | 1/1960 | Wallshein | |
| 3,075,287 A | 1/1963 | Weinger | |
| 3,203,098 A | 8/1965 | Petraitis | |
| 3,250,003 A * | 5/1966 | Collito | 433/9 |
| 3,262,207 A | 7/1966 | Kesling | |
| 3,353,271 A | 11/1967 | Blechman | |
| 3,423,833 A | 1/1969 | Pearlman | |
| 3,435,527 A | 4/1969 | Kesling | |
| 3,464,113 A | 9/1969 | Silverman et al. | |
| 3,597,845 A | 8/1971 | Russ | |
| 3,721,005 A | 3/1973 | Cohen | |
| 3,738,005 A * | 6/1973 | Cohen et al. | 433/3 |
| 3,772,787 A | 11/1973 | Hanson | |
| 3,946,488 A | 3/1976 | Miller et al. | |
| 4,014,096 A | 3/1977 | Dellinger | |
| 4,077,126 A | 3/1978 | Pletcher | |
| 4,134,208 A | 1/1979 | Pearlman | |

(Continued)

*Primary Examiner* — Todd Manahan
*Assistant Examiner* — Yogesh Patel
(74) *Attorney, Agent, or Firm* — Dascenzo Intellectual Property Law, P.C.

(57) ABSTRACT

Systems, methods, and apparatus for creating a mold of a patient's teeth to which are installed orthodontic appliances with a support assembly bonded to a tooth. The appliances may include a corresponding corrective assembly with a wire engaging portion removably coupled to the support assembly. The systems and methods may include removing a corrective assembly from a support assembly, applying unset molding compound to the patient's teeth and corresponding support assemblies, setting the molding compound into a mold, and nondeformably removing the mold from the patient's mouth. The support assemblies may include a marker portion to indicate the position of the wire engaging portion of a corrective assembly that may be removed prior to making a mold and/or installed after making the mold. Marker assemblies adapted to removably engage a support assembly, and including such a marker portion, may be temporarily coupled to support assemblies prior to making a mold.

28 Claims, 4 Drawing Sheets

U.S. PATENT DOCUMENTS

| | | | |
|---|---|---|---|
| 4,144,642 | A | 3/1979 | Wallshein |
| 4,171,568 | A | 10/1979 | Forster |
| 4,197,642 | A | 4/1980 | Wallshein |
| 4,243,387 | A | 1/1981 | Prins |
| 4,248,588 | A | 2/1981 | Hanson |
| 4,272,240 | A | 6/1981 | Glassman |
| 4,302,532 | A | 11/1981 | Wallshein |
| 4,353,692 | A | 10/1982 | Karrakussoglu |
| 4,371,337 | A | 2/1983 | Pletcher |
| 4,419,078 | A | 12/1983 | Pletcher |
| 4,483,674 | A | 11/1984 | Schutz |
| 4,487,581 | A | 12/1984 | Adler |
| 4,492,573 | A | 1/1985 | Hanson |
| 4,496,317 | A | 1/1985 | Hulsey |
| 4,519,779 | A | 5/1985 | Lieb |
| 4,531,911 | A | 7/1985 | Creekmore |
| 4,559,012 | A | 12/1985 | Pletcher |
| 4,561,844 | A | 12/1985 | Bates |
| 4,597,739 | A * | 7/1986 | Rosenberg ..................... 433/16 |
| 4,614,497 | A | 9/1986 | Kurz |
| 4,634,661 | A | 1/1987 | Cavallaro |
| 4,655,708 | A | 4/1987 | Fujita |
| 4,676,746 | A | 6/1987 | Klapper |
| 4,698,017 | A | 10/1987 | Hanson |
| 4,712,999 | A | 12/1987 | Rosenberg |
| 4,786,242 | A | 11/1988 | Barsk |
| 4,878,840 | A | 11/1989 | Reynolds |
| 5,032,080 | A | 7/1991 | Hakansson et al. |
| 5,044,945 | A | 9/1991 | Peterson |
| 5,064,369 | A | 11/1991 | Kawaguchi |
| 5,094,614 | A | 3/1992 | Wildman |
| 5,186,623 | A * | 2/1993 | Breads et al. .................... 433/6 |
| 5,263,859 | A | 11/1993 | Kesling |
| 5,302,121 | A | 4/1994 | Gagin |
| 5,322,435 | A | 6/1994 | Pletcher |
| 5,356,288 | A | 10/1994 | Cohen |
| 5,366,372 | A | 11/1994 | Hansen et al. |
| 5,439,379 | A | 8/1995 | Hansen |
| 5,562,444 | A | 10/1996 | Heiser et al. |
| 5,711,666 | A | 1/1998 | Hanson |
| 5,746,593 | A | 5/1998 | Forster |
| 5,857,850 | A | 1/1999 | Voudouris |
| 5,902,104 | A | 5/1999 | Yamada |
| 5,954,502 | A | 9/1999 | Tuenge et al. |
| 6,139,317 | A | 10/2000 | Goldshmied |
| 6,142,775 | A | 11/2000 | Hansen et al. |
| 6,193,508 | B1 | 2/2001 | Georgakis |
| 6,220,857 | B1 | 4/2001 | Abels |
| 6,264,469 | B1 | 7/2001 | Moschik |
| 6,302,688 | B1 | 10/2001 | Jordan et al. |
| 6,358,045 | B1 | 3/2002 | Farzin-Nia et al. |
| 6,582,226 | B2 | 6/2003 | Jordan et al. |
| 6,632,088 | B2 | 10/2003 | Voudouris |
| 6,655,957 | B2 | 12/2003 | Abels et al. |
| 6,659,766 | B2 | 12/2003 | Abels et al. |
| 6,733,286 | B2 | 5/2004 | Abels et al. |
| 7,137,812 | B2 | 11/2006 | Cleary et al. |
| 2002/0110777 | A1 | 8/2002 | Abels et al. |
| 2003/0003415 | A1 | 1/2003 | Kim et al. |
| 2003/0198913 | A1 | 10/2003 | Cinader, Jr. et al. |
| 2004/0083611 | A1 | 5/2004 | Rubbert et al. |
| 2004/0185410 | A1 | 9/2004 | Lai |
| 2005/0277084 | A1 * | 12/2005 | Cinader et al. ................. 433/20 |
| 2006/0014116 | A1 | 1/2006 | Maijer et al. |
| 2008/0241782 | A1 | 10/2008 | Abels et al. |

* cited by examiner

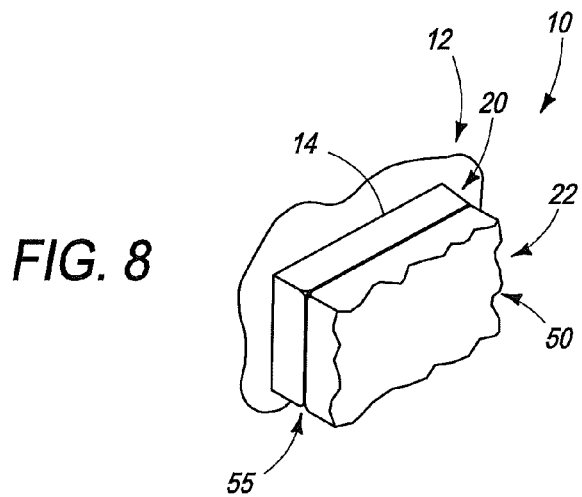
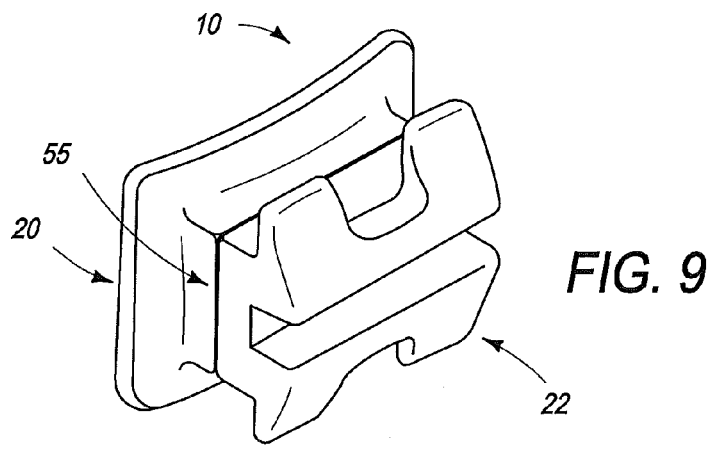
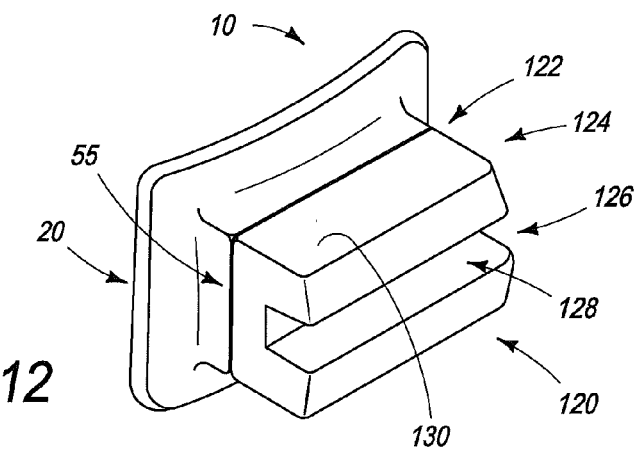

ORTHODONTIC TREATMENT METHODS, SYSTEMS AND APPARATUS FOR USE THEREWITH

RELATED APPLICATIONS

The present application is a continuation patent application that claims priority under 35 U.S.C. §120 to U.S. patent application Ser. No. 11/708,769, which is entitled "Orthodontic Treatment Methods, Systems and Apparatus for Use Therewith," which was filed on Feb. 20, 2007, and which issued on Aug. 10, 2010 as U.S. Pat. No. 7,771,640. U.S. patent application Ser. No. 11/708,769 claims priority to similarly entitled U.S. Provisional Patent Application Ser. No. 60/774,701, which was filed on Feb. 17, 2006. The complete disclosures of the above-identified patent applications are hereby incorporated by reference for all purposes.

TECHNICAL FIELD

The present disclosure is related generally to the field of orthodontia, and more particularly to methods and apparatus for orthodontic treatment.

BACKGROUND OF THE DISCLOSURE

During orthodontic treatment, it is often desirable, and in some cases necessary, to create molds or other impressions of an orthodontic patient's teeth. When conventional orthodontic brackets are not mounted on the patient's teeth, a variety of suitable molding compounds and impression methods may be used. However, when conventional orthodontic brackets are installed on the patient's teeth, the range of suitable molding compounds and impression methods is much more limited, especially when it is desirable or necessary to accurately reproduce the position of the archwire-receiving slot, which is defined by the orthodontic brackets, relative to the patent's teeth.

Many conventional molding compounds, or materials, that are suitable for creating molds or impressions of a patient's teeth prior to the installation of orthodontic brackets are unsuitable for creating impressions of the patient's teeth while the brackets are installed. While these compounds, an example of which is polyvinylsiloxane, are suitable for creating very accurate molds of the patient's teeth, including impressions that are suitable for destructive scanning, or imaging, processes, the molding compounds set, or cure, so solidly that they are likely to debond (detach or otherwise remove) orthodontic brackets from the patient's teeth, damage the orthodontic brackets, and/or deform or otherwise damage or distort the mold during the removal process from the patient's teeth (and installed orthodontic brackets). Specifically, the bracket is typically connected to a patient's tooth with an adhesive that is not strong enough to withstand the imparted forces as the set molding material, or mold, which also extends around the brackets, is drawn away from the patient's teeth. As a result, this removal of the mold may debond the bracket from the tooth as the mold is removed from the patient's teeth. Such a rigid impression material is also prone to solidifying around the undercuts, wings, or other projecting portions of an orthodontic bracket and thereby prevent nondeformable removal of the mold without damaging the bracket or the mold.

Other molding compounds are suitable for making impressions of the patient's teeth even after the installation of orthodontic brackets, but these molding compounds are formed from materials that are sufficiently flexible, soft, and/or deformable that they are not suitable to create molds for use in some orthodontic applications, such as applications where very accurate, or detailed, representations of the patient's teeth and attached brackets are needed. One example of such a compound is alginate, a natural polymer. Such materials, once set, are likely to tear, deform, or otherwise distort during removal of the set molding compound, thereby rendering the resulting mold unable to accurately reproduce the position of the brackets and/or archwires relative to the patient's teeth.

A further method of creating very accurate representations of a patient's teeth after orthodontic brackets are installed involves the use of CT scanners or other intra-oral scanners that create images of the patient's teeth, including any attached orthodontic brackets. These images may be used to make electronic or other models or representations of the patient's teeth and the attached orthodontic brackets. However, this scanning process requires expensive scanning equipment and takes considerable time and practitioner attention (especially when compared to using molding compounds).

SUMMARY OF THE DISCLOSURE

The present disclosure is directed to systems, methods, and apparatus for orthodontic treatment. The methods include methods for creating accurate impressions and molds of an orthodontic patient's teeth to which orthodontic brackets are mounted. In some embodiments, the methods accurately and reproducibly produce impressions of the teeth and brackets, including archwire slots or other wire engaging structure defined by the brackets, without damaging or debonding the brackets, or damaging the mold, as the mold is nondeformably removed from the patient's teeth. In some embodiments, the methods include utilizing orthodontic brackets that include a base, or support assembly, which is bonded to a patient's tooth, and a corrective assembly, which is removably and replaceably coupled to the support assembly and which includes a wire engaging portion, such as an archwire-receiving slot. Such a corrective assembly is utilized to impart corrective forces to the patient's teeth upon receipt of an archwire in the wire engaging portion. In some methods that utilize these multi-piece brackets, the corrective assemblies are intentionally removed prior to the molding process, with the support assemblies indicating the position of the assembled brackets (and optionally the corresponding archwire-receiving slots) relative to the patient's teeth. However, in some methods, the corrective assemblies may be left coupled to the support assemblies, and debonded after a mold is created as the mold is nondeformably removed from the patient's teeth.

In some embodiments, a temporarily installed marker assembly may be adapted to define or otherwise indicate the position of the archwire-receiving slot during the molding process, but may be adapted to be unsuitable for use during tooth-aligning use of the brackets. In such embodiments, a marker assembly, which may also be referred to as a "temporary corrective assembly," a "slot indicator," and/or a "slot marker," may include a marker coupling portion that is adapted to releasably engage a support assembly and a marker portion that is adapted to indicate, when the marker assembly is engaged with the support assembly, the archwire-receiving slot (or other wire engaging portion or structure) of the support assembly's corresponding corrective assembly.

In at least the above embodiment, the marker assembly may be adapted to form a portion of the mold, or model, of the patient's teeth. In other embodiments, the marker assembly may be adapted to remain coupled to the support assembly after nondeformably removing the mold. Either result may be achieved, for example, by adapting a marker assembly, when engaged with the support assembly, to establish a bond of a desired bond strength relative to that established when the support assembly is engaged with its corresponding corrective assembly. In either case, such marker assemblies may be defined by a perimeter surface that is free of projections extending in a direction generally parallel to the surface of the portion of the tooth to which the support assembly is bonded. Such a configuration may, for example, assist removal of a set mold without contemporaneously removing the marker assemblies as the mold is drawn away from the patient's teeth.

Accordingly, some methods may include, prior to the molding process, removing a corrective assembly from a support assembly, and coupling a marker assembly to the support assembly. The marker assembly may be removed as the set mold is nondeformably removed from the patient's teeth, or separately and subsequently removed. The removed corrective assembly, or another corrective assembly, may be recoupled to the support assembly, and the archwire reattached, to resume orthodontic treatment.

These and other exemplary methods may include utilizing any of the above-described brackets and/or marker assemblies to create accurate models or representations of the patient's teeth. In some embodiments, the models accurately record, or reproduce, the position of the brackets and/or archwire relative to the patient's teeth. The methods may further include thereafter utilizing the model in orthodontic treatment, such as to create computer-modeled and/or computer-created corrective assemblies and/or archwires.

BRIEF DESCRIPTION OF THE DRAWINGS

FIG. 8 is a fragmentary, schematic perspective view of an assembled orthodontic appliance that may be used with systems and methods according to the present disclosure.

FIG. 9 is an illustrative, somewhat less schematic isometric view of an assembled orthodontic appliance that may be used with systems and methods according to the present disclosure.

FIG. 12 is an isometric view showing an illustrative example of an orthodontic appliance that includes a marker assembly that may be used with systems and methods according to the present disclosure.

DETAILED DESCRIPTION AND BEST MODE OF THE DISCLOSURE

Figure 1:
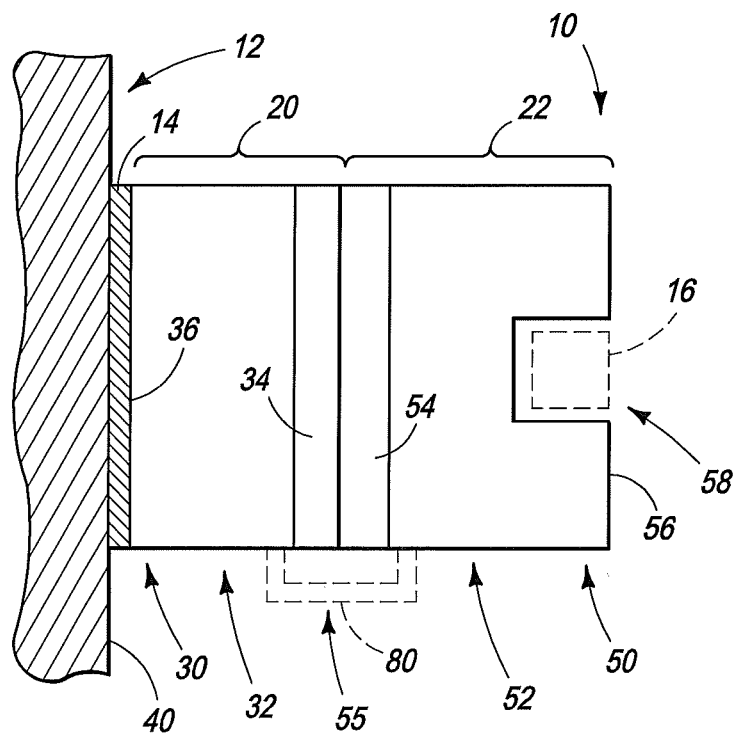
FIG. 1 is a schematic diagram showing various components of an illustrative example of a multi-piece, reusable orthodontic appliance that may be used with systems and methods according to the present disclosure.

The present disclosure is related to orthodontic appliances, including multi-piece (i.e., two or more piece) orthodontic brackets, and systems and methods for utilizing these brackets for obtaining molds, impressions, and other representations of an orthodontic patient's teeth after installation of orthodontic brackets to the patient's teeth. In the context of this disclosure, the term "patient's teeth" is used to indicate all or some of the teeth of an orthodontic patient, one or more of which have an orthodontic bracket installed thereon. For example, molds may be made from a patient's complete set of upper or lower teeth, but may also be made from a subset of a patient's upper or lower teeth, or even a single tooth. Molds may also be made from a combination of at least one of a patient's teeth that includes an orthodontic bracket and at least one of a patient's teeth that does not include an orthodontic bracket. The systems and methods of the present disclosure include the use of orthodontic brackets, or appliances, that each include a base portion, or support assembly, that is adapted to be bonded to a tooth, and a corrective assembly, or bracket portion, which defines an archwire-receiving slot or other structure to engage an archwire, and which is adapted to be releasably coupled to the support assembly.

In use, to apply tooth-aligning or other corrective forces to an orthodontic patient's teeth, a support assembly is adhesively (or otherwise suitably) bonded to a patient's tooth, the corrective assembly is coupled to the support assembly, and an archwire is received and secured into the archwire-receiving slot. Each coupled set of a support assembly and a corrective assembly collectively may be referred to as an orthodontic bracket or an orthodontic appliance. The corrective assembly may be coupled to the support assembly by any suitable fastening mechanism, or coupling assembly. While not required to all embodiments, the coupling assembly may secure the corresponding support assembly and corrective assembly together with less force than the adhesive, or other mechanism, secures the support assembly to the patient's tooth. In other words, the appliance may be adapted to decouple the corrective assembly from the support assembly responsive to an applied force, such as an unintentional force that otherwise might debond the entire orthodontic bracket from the patient's tooth and/or an intentional force that is intended to decouple the corrective assembly without debonding the support assembly from the patient's tooth. Illustrative, exclusive examples of suitable orthodontic appliances that may (but are not required to be) used with the systems and methods of the present disclosure are disclosed in U.S. patent application Ser. No. 11/260,074, which is entitled "Reusable Multi-piece Orthodontic Appliances," was filed on Oct. 26, 2005, and the complete disclosure of which is hereby incorporated by reference for all purposes.

When it is necessary or desirable to create a mold or other impression, image, or representation of the patient's teeth, mouth, or portion thereof, molding compound may be applied to the orthodontic patient's teeth, including one or more teeth to which an orthodontic appliance has been installed. Optionally, the archwire may be removed from the archwire-receiving slots of corrective assemblies prior to applying the molding compound. Additionally, and as explained in more detail below, the corrective assemblies may be uncoupled from the support assemblies, optionally with the archwire removed from the archwire-receiving slots of the corrective assemblies prior to or after uncoupling of the corrective assemblies from the support assemblies. With the corrective assemblies and archwire removed from the patient's mouth, a mold or other representation of the patient's teeth may be obtained without the risk of the corrective assemblies being damaged and/or debonded from the patient's teeth, and/or the mold being damaged or deformed by the corrective assemblies. Similarly, molding compounds or materials, such as polyvinylsiloxane dental impression material, among others, that are adapted to produce very accurate impressions, such as by firmly hardening or otherwise curing, may be used even though they could not reliably (or at all) be used with conventional orthodontic brackets that include a monolithic bracket structure that is adhesively bonded to a tooth and which includes an archwire-receiving slot.

Although a mold created from a patient's teeth to which only support assemblies are installed (i.e., with corrective assemblies removed) would not include an impression of the corrective assemblies of the multi-piece orthodontic appliances, the position thereof, and/or of the corresponding archwire-receiving slot or other wire engaging portion, may be determined. For example, the dimensions of a corrective assembly, including the relative position of the archwire-receiving slot therein, are known, and thus the position of the archwire-receiving slot and/or the corrective assembly relative to the patient's teeth can be determined from the mold from the impression of the support assembly. As the term is used herein, "position" includes any aspect of the three-dimensional configuration or orientation of the relevant structure. In some applications, this term may be used to refer to the relative orientation of the archwire-receiving slot relative to a portion of a patient's tooth to which the correctively assembly is, was, and/or is intended to be, bonded.

In some embodiments, the support assembly may be adapted to include a marker portion, such as an indicia, landmark, projection or recess, or other structural, physical, or detectable feature adapted to indicate the relative position of the corresponding archwire-receiving slot. In some embodiments, the orientation of the support assembly's perimeter may define or otherwise indicate the position of the archwire-receiving slot of the corresponding corrective assembly. In some embodiments, the support assembly may be shaped to have at least a perimeter surface that is free from lateral projections or other regions that may impair or otherwise interfere with obtaining (and/or nondeformably removing) accurate molds of the support assembly. In such embodiments, a support assembly may be provided with a marker portion prior or subsequent to installation to a patient's tooth. Illustrative, non-exclusive examples include affixing an outwardly projecting indicator to a previously installed support assembly, shaping a perimeter surface of a support assembly during fabrication or otherwise prior to bonding to a patient's tooth, and so forth. In some embodiments, the marker portion additionally or alternatively is configured to be detected by a CT scanner, radiofrequency scanner, or other imaging device, such as by the color of the marker portion, luminescence of the marker portion, radiative property of marker portion, etc. In some embodiments, the marker portion is adapted to be inserted or otherwise installed or coupled to the archwire-receiving slot of one or more of the corrective assemblies of the bracket assemblies on the patient's teeth of which the mold is to be formed.

In some embodiments, a temporarily installed marker assembly that is adapted for use with the orthodontic appliances (or brackets) may include a marker portion, as described above, that is adapted to define, or otherwise indicate or represent the position of, the archwire-receiving slot (or other wire engaging portion) during the molding process, but such a marker assembly may be adapted not to be used during tooth-aligning use of the brackets. For example, the marker assembly may be configured to be coupled to a support assembly and may include an archwire-receiving slot that, when the marker assembly is coupled to the support assembly, corresponds to the position of the archwire-receiving slot of the corrective assembly that was removed from the support assembly and/or which is intended to be coupled to the support assembly. In some embodiments, the marker assembly may be similar in shape to the corrective assembly except that it is free from wings, projections or other structures that would be present in an actual orthodontic bracket or corrective assembly to retain (or assist in retaining) an archwire in the archwire-receiving slot. For example, the marker assemblies may be free from projections that extend, in a spaced-apart relationship, generally parallel to the surface of the portion of a tooth to which the corresponding support assembly is secured.

In some embodiments, the marker assembly is adapted to form a portion of the mold, or model, of the patient's teeth, while in others it is adapted to remain coupled to the support assembly subsequent to and separate from removal of the set molding compound. In the former example, the marker assemblies may be coupled to the corresponding support assemblies by the coupling assembly that is used to secure the corrective assemblies to the support assemblies, or may include similar coupling structure adapted to establish, when the marker assembly is engaged with the support assembly, a bond strength substantially equivalent to or greater than that established between the corrective assembly and the support assembly. In some embodiments, including embodiments where the marker assembly is designed to form part of the mold, it may be desirable to utilize a different coupling assembly or mechanism or to configure the marker assemblies to be decoupled from the support assemblies as the molding compound is drawn away from the patient's teeth. In other words, a comparably lower strength bond or coupling may be used than that used to couple the support assembly to a corrective assembly.

In some embodiments, the marker assembly may be formed from plastic or another suitable material for use in destructive imaging/scanning processes, which may be utilized to generate images from the mold, and in some embodiments, the marker assemblies may be colored to be more readily detected by imaging devices. As an illustrative example, some CT scanners are best adapted to detect white-colored surfaces.

The produced mold may be utilized for a variety of orthodontic applications. Illustrative, non-exclusive examples of these applications include forming retainers and/or molded orthodontic devices (such as Invisalign®-type devices), producing detailed models of the patient's teeth (which optionally may include attached orthodontic appliances or other brackets), creating electronic (computer-generated) models of the patient's teeth, etc. A further illustrative, non-exclusive example of an application for the produced mold is to determine archwire-receiving slot positions for patients of SureSmile™ therapeutics, Insignia™ systems, or other applications where it is necessary to know the precise position of the archwire-receiving slots in an orthodontic patient's mouth. SureSmile™ therapeutics are available from Orametrix of Richardson, Tex. SureSmile™ therapeutics require precise electronic/digital 3-D models of a patient's teeth, with these images being utilized for computer-driven (i.e., robotic) creation of archwires for orthodontic treatment. Insignia™ custom orthodontic systems are available from Ormco Corporation of Orange, Calif.

An illustrative, non-exclusive example of a multi-piece, reusable orthodontic appliance that may be used with the systems and methods of the present disclosure is schematically illustrated in FIG. 1 and generally indicated at 10. Appliance 10 is generally configured to be bonded to a tooth 12, such as via bonding media 14, and more specifically to receive or otherwise engage an archwire 16 and transmit corrective forces from the archwire to the tooth. In particular, appliance 10 includes a support assembly 20 and a corrective assembly 22. As explained in greater detail herein, support assembly 20 is adapted to be bonded or otherwise secured to a tooth, and corrective assembly 22 is adapted to receive the archwire and to direct corrective forces exerted by the archwire to the tooth. Support assembly 20 and corrective assembly 22 are configured to be releasably coupled, or engaged, together to collectively form orthodontic appliance 10. However, corrective assembly 22 is configured to disengage from support assembly 20 in response to a suitable disengaging force being applied to the appliance, such as to the corrective assembly and/or the subsequently described engagement assembly.

In FIG. 1, the support assembly and corrective assembly are schematically illustrated as being coupled together by an engagement assembly 55. Engagement assembly 55 is adapted to releasably and repeatedly couple the support and corrective assemblies together to form an assembled orthodontic appliance, or bracket, 10. Engagement assembly 55 may, but is not required in all embodiments to, include first and second coupling portions, such as indicated at 34 and 54 in FIG. 1. As illustrated, first coupling portion 34 is associated with support assembly 20 and second coupling portion 54 is associated with corrective assembly 22.

Engagement assembly 55 of an orthodontic appliance 10 according to the present disclosure, or more specifically first coupling portion 34 and/or second coupling portion 54, may take any appropriate form, and may include any manner of components including mechanical linkages, magnetic linkages, adhesive linkages, and so forth, that are collectively configured to establish a connection or other engagement of the corrective assembly with the support assembly such that the engagement assembly will release responsive to a force exceeding a predetermined value applied to the corrective assembly. Some embodiments may, but are not required to, include combinations of such components. For example, some embodiments that include coupling portions that are adapted to fit together in a snap fit relationship may also include a magnetic linkage, such as a magnetically attractive part on one of the coupling portions and a magnetically attracted part on the other coupling portion.

Engagement assembly 55 may be adapted to release the corrective assembly from the support assembly responsive to a suitable force applied to the orthodontic appliance, such as to the corrective assembly and/or engagement assembly. In some embodiments, the engagement assembly may be configured to release the corrective assembly from the support assembly when a suitable force is applied to a predetermined region of the engagement assembly and/or in a predetermined direction, while in other embodiments, the particular direction and/or region may not be critical. As discussed in more detail herein, the engagement assembly of orthodontic appliances according to the present disclosure may be, but is not required to be, coupled together by a weaker bond, or weaker attachment mechanism, than the bond or mechanism that couples the support assembly to a tooth. Therefore, the applied force will tend to disengage the corrective assembly from the support assembly, by disengaging the engagement assembly, rather than removing the entire appliance from a patient's tooth. Accordingly, it is within the scope of the present disclosure that the corrective assembly is adhesively bonded to the support assembly by a suitable bonding agent, or media. In such a configuration, the bonding agent preferably establishes a weaker bond between the corrective and structural assemblies than the bonding media that secures the corrective assembly to a tooth or tooth-encircling band. In other embodiments, and as discussed, the engagement assembly establishes a mechanical coupling between the support and corrective assemblies.

The components and/or structural features of support assembly 20 and corrective assembly 22 may be configured as desired to enable repeated engagement and disengagement of the assemblies, without destruction or deterioration to any of the components of the appliance caused by engaging or disengaging the coupling portions. In particular, the first and second coupling portions may be configured to be reusable after being disengaged, for example by being fabricated to remain structurally intact upon engagement and disengagement. Thus, for example, an orthodontist may install several appliances 10 to the teeth of a patient, for orthodontic treatment, without having to replace components that become damaged due to disengagement during the period of the treatment. Instead, the orthodontist, or in some embodiments even the patient, may reengage any detached components, resuming treatment. Accordingly, the components, or assemblies, of orthodontic appliances according to the present disclosure are adapted to be repeatedly disengaged and reengaged without destruction of the components, or assemblies. For example, the corrective assemblies of an orthodontic appliance according to the present disclosure may be adapted to be disengaged from a corresponding support assembly that is coupled to a tooth in a patient's mouth. Should the corrective assembly be disengaged from the support assembly, such as described herein, neither the support assembly nor the corrective assembly is damaged or otherwise rendered unable to be used as part of an orthodontic appliance 10 according to the present disclosure. Accordingly, the assemblies may be reengaged, and thereby reused. However, it is not a requirement for an orthodontic appliance 10 to always have its support and corrective assemblies reengaged for reuse of both assemblies in all embodiments and at all times. For example, during orthodontic treatment, in some situations it may be desirable to intentionally disengage the support and corrective assemblies of an orthodontic appliance 10 according to the present disclosure and to reengage the support assembly, which is still coupled to a tooth, to the same or a different corrective assembly. The above-described systems and methods for forming detailed molds of a patient's teeth are an example of such a situation. It is further within the scope of the present disclosure, though not required, that the disengaged corrective assembly may be reengaged with a different support assembly for further use. Therefore, orthodontic appliances 10 may be described as being "reusable" even though reuse is not required to all embodiments or in all applications.

Orthodontic appliances 10 according to the present disclosure have also been described as being "multi-piece" orthodontic appliances. As used herein, "multi-piece" refers to an orthodontic appliance that is a composite structure consisting of at least two components, namely, at least support assembly 20 and corrective assembly 22, that are configured to be releasably coupled together. Therefore, orthodontic appliances according to the present disclosure may include two components, three components, four components, or more. The two or more inter-engageable components define an orthodontic bracket that is secured to a tooth and which includes an archwire-receiving slot. The support and corrective assemblies may be single-piece components, such as which include a monolithic body, or base portion. However, it is also within the scope of the present disclosure that the support and coupling assemblies themselves may be composite structures consisting of two or more separable subcomponents, or that the various components and structural features of each assembly may be integrally formed.

For example, and with continuing reference to FIG. 1, support assembly 20 includes a tooth engaging portion 30 that is adapted to be bonded to a tooth 12. The support assembly further includes a support portion 32 extending from the tooth engaging portion generally away from the tooth. As illustrated, the support portion includes a first coupling portion 34 that is adapted to be releasably coupled to, or engaged with, corrective assembly 22.

Figure 2:
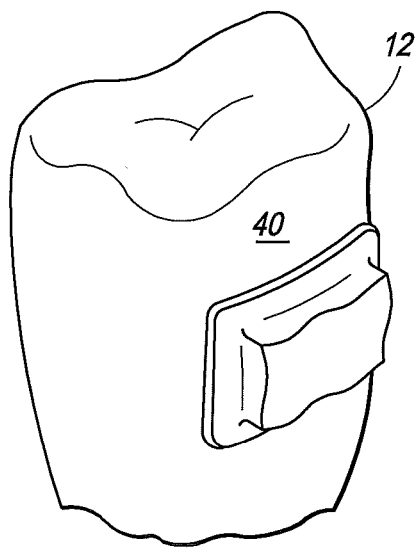
FIG. 2 is a fragmentary isometric view showing an exemplary tooth engaging portion of an orthodontic appliance bonded directly to a tooth surface.
Figure 3:
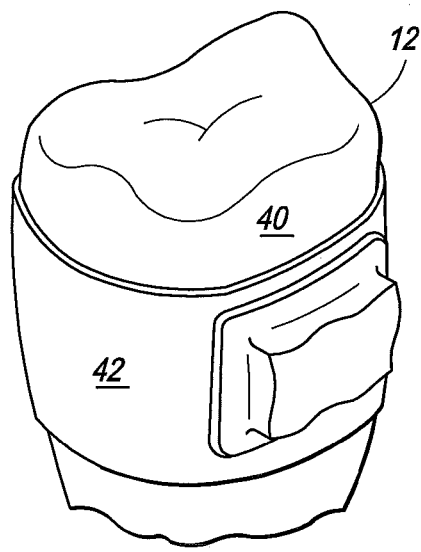
FIG. 3 is a fragmentary isometric view showing an exemplary tooth engaging portion of an orthodontic appliance bonded to a band that encircles a tooth.

Tooth engaging portion 30 may include a tooth-facing rear surface 36, which may be configured as desired for being bonded or otherwise secured to tooth 12, such as with bonding media 14. As used herein, the front surface, or region, of an assembly or component generally refers to the surface or region that is adapted to face away from the tooth to which the corresponding appliance 10 is coupled during use, while the rear surface, or region, of an assembly or component generally refers to the surface or region that is adapted to face the tooth to which the corresponding appliance 10 is coupled during use of the appliance. Direct contact between the tooth-facing rear surface of the tooth engaging portion is not required. Accordingly, the tooth engaging portion may additionally or alternatively be referred to as a tooth-facing portion 30, and/or a portion 30 that is adapted to be bonded to a tooth. For example, rear surface 36 may be adapted to be bonded with a bonding media, such as a suitable cement and/or other adhesive, either directly to a tooth surface 40 as shown in FIG. 2, or to a tooth band 42 that is secured around tooth 12, as shown in FIG. 3. As such, rear surface 36 may be generally planar or contoured, smooth or textured, and/or may include ribs or other structure configured to secure the tooth engaging portion 30 to the tooth to achieve a bond of any desired strength.

As illustrated in FIG. 1, support portion 32 extends from tooth engaging portion 30, generally away from tooth 12. First coupling portion 34 is situated on support portion 32, and as such may be integrally formed with support portion 32, or may be a separate structure that is coupled to the support portion, such as during fabrication, prior to installation of the appliance in a patient's mouth, or even during installation, by any appropriate means, such as which may include mechanical, magnetic, and/or other suitable types of linkages, adhesive bonding, and so forth.

Corrective assembly 22 includes a wire engaging portion 50 that is adapted to receive archwire 16, a base portion 52 extending from the wire engaging portion and generally away from the archwire, and a second coupling portion 54 on the base portion. The wire engaging portion of orthodontic appliance 10 may be configured as desired to receive or otherwise accommodate an archwire, and the configuration may assist direction of corrective forces to the tooth. Thus, although other methods of accommodating an archwire are possible, wire engaging portion 50 may include a front surface 56 with an archwire, or archwire-receiving, slot 58, into which the archwire may be seated. Wire engaging portion 50 may further include structure adapted to secure archwire 16 in place with respect to orthodontic appliance 10, such as suitable structure to retain the archwire within archwire slot 58.

Figures 4, 5:
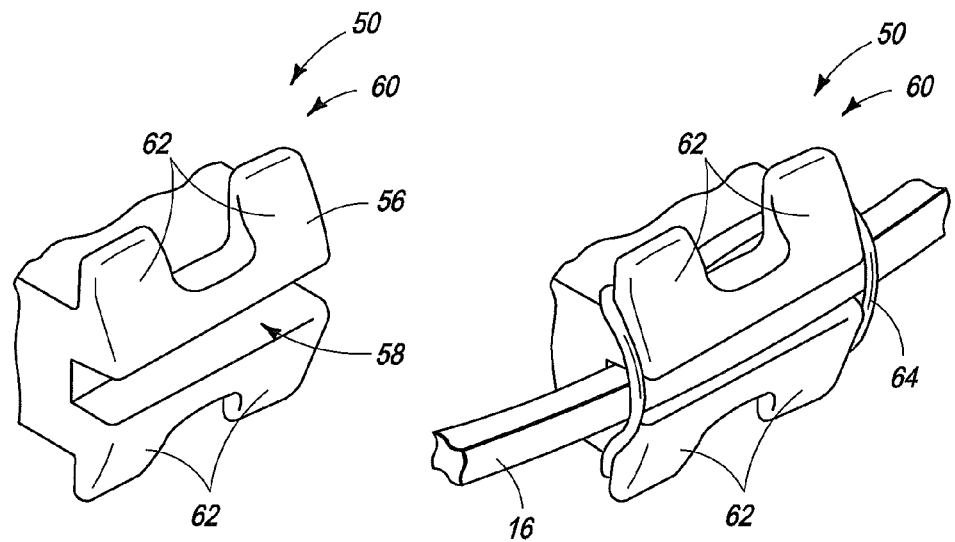
FIG. 4 is a fragmentary isometric view showing an exemplary ligating wire engaging portion of an orthodontic appliance, such as may be used with orthodontic appliances according to the present disclosure.
FIG. 5 is a fragmentary isometric view showing the ligating wire engaging portion of FIG. 4 engaging an archwire.

For example, wire engaging portions 50 according to the present disclosure may include structural features of, or similar to, a ligating orthodontic bracket. An example of such a wire engaging portion 50 is shown in FIGS. 4 and 5 and is indicated generally at 60. In FIG. 4, an exemplary ligating wire engaging portion 60 is shown to include a front surface, or region, 56 featuring an archwire-receiving slot 58 and tie wings 62 that are arranged adjacent to the archwire slot, such as the sets of tie wings shown in FIG. 4 on either side of the archwire slot. As seen in FIG. 5, tie wings 62 may be used in coordination with a ligature wire, elastic band, or other securing device 64 in order to secure archwire 16 in a desired position with respect to the ligating wire engaging portion.

Figures 6, 7:
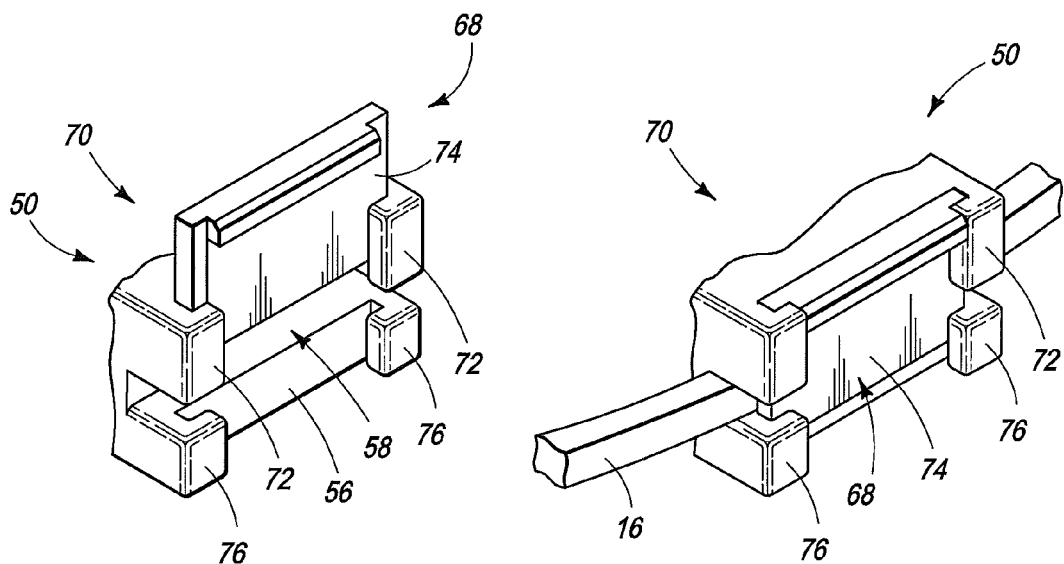
FIG. 6 is a fragmentary isometric view showing an exemplary self-ligating wire engaging portion of an orthodontic appliance, such as may be used with orthodontic appliances according to the present disclosure.
FIG. 7 is an isometric view showing the self-ligating wire engaging portion of FIG. 6 engaging an archwire.

It is also within the scope of the present disclosure that the wire engaging portion may include structural features of, or similar to, a self-ligating orthodontic bracket. For example, the wire engaging portion may include a releasable clamp, gate, clasp, or other suitable locking structure that is adapted to releasably secure an archwire within the archwire slot. An illustrative example of a self-ligating wire engaging portion is shown in FIGS. 6 and 7 and is generally indicated at 70. In FIG. 6, the exemplary self-ligating wire engaging portion 70 is shown to include a front surface 56 with an archwire slot 58 and a pair of support arms 72 disposed on one side of the archwire slot. Support arms 72 support a slidable locking member 74. As seen in FIG. 7, slidable locking member 74 may be moved to engage a pair of receiving arms 76 disposed on the opposite side of the archwire slot, to secure archwire 16 in place with respect to the self-ligating wire engaging portion. Slidable locking member 74 essentially allows the self-ligating wire engaging portion to retain the archwire without the use of ligatures that are adapted to secure the archwire within the archwire slot. Member 74 may be described as being selectively slid, or otherwise moved, between a first, or open, configuration in which the member is positioned to permit the archwire to be inserted into and removed from the archwire slot, and a second, or locked, configuration in which the member extends sufficiently across the archwire slot to prevent removal of the archwire through the slot. It is within the scope of the present disclosure that other locking structures may be used in self-ligating wire engaging portions 70 according to the present disclosure. As an illustrative example, some locking structures may be adapted to pivot between locked and unlocked configurations, in which the locking structures are respectively positioned to retain or release the archwire from the archwire slot of a wire engaging portion to which the locking structure is secured.

Illustrative, non-exclusive examples of ligating orthodontic brackets that disclose structures and/or components that may be used with ligating wire engaging portions 70 according the present disclosure are disclosed in U.S. Pat. Nos. 6,302,688, 6,582,226, 4,878,840, 3,772,787, 4,248,588, 4,492,573, 4,614,497, 4,698,017, 1,280,628, 1,821,171, and 3,435,527, the complete disclosures of which are hereby incorporated herein by reference for all purposes. Illustrative, non-exclusive examples of self-ligating orthodontic brackets that disclose structures and/or components that may be used with self-ligating wire engaging portions 70 according to the present disclosure are disclosed in U.S. Pat. Nos. 6,659,766, 6,655,957, 6,358,045, 6,193,508, 5,857,850, 5,711,666, 5,562,444, 5,322,435, 5,094,614, 4,559,012, 4,531,911, 4,492,573, 4,419,078, 4,371,337, 4,077,126, 4,144,642, 4,248,588, 4,698,017, 3,772,787, 4,559,012, 4,561,844, 4,655,708, 4,419,078, 4,197,642, 4,712,999 and 4,171,568, the complete disclosures of which are hereby incorporated by reference herein for all purposes. Additional examples of orthodontic brackets that include features that may be incorporated into orthodontic appliances according to the present disclosure are disclosed in U.S. Pat. No. 6,632,088, the complete disclosure of which is hereby incorporated by reference for all purposes. The above-incorporated examples of conventional ligating and self-ligating brackets may also be utilized with embodiments of orthodontic appliances according to the present disclosure that include at least a support assembly that is adapted to be releasably coupled (directly or indirectly) to a conventional orthodontic bracket that includes a monolithic body portion and/or which is otherwise adapted to be utilized without an orthodontic appliance according to the present disclosure. Additional examples of conventional orthodontic brackets that may be incorporated into orthodontic appliances and the systems and methods of the present disclosure are 3M, Sybron, GAC, and American or Rocky Mountain orthodontic brackets.

FIGS. 8 and 9 provide graphical examples of assembled appliances 10. FIG. 8 schematically depicts an appliance with a support assembly 20 to which a corrective assembly 22 is coupled by engagement assembly 55, with the corrective assembly being shown in fragmentary to present any suitable archwire-receiving structure. In FIG. 8, the support assembly is shown secured to a patient's tooth 12, such as with bonding media 14. FIG. 9 less schematically represents an appliance 10 that generally resembles a conventional ligating orthodontic bracket, such as discussed above with respect to FIGS. 4 and 5.

Figure 10:
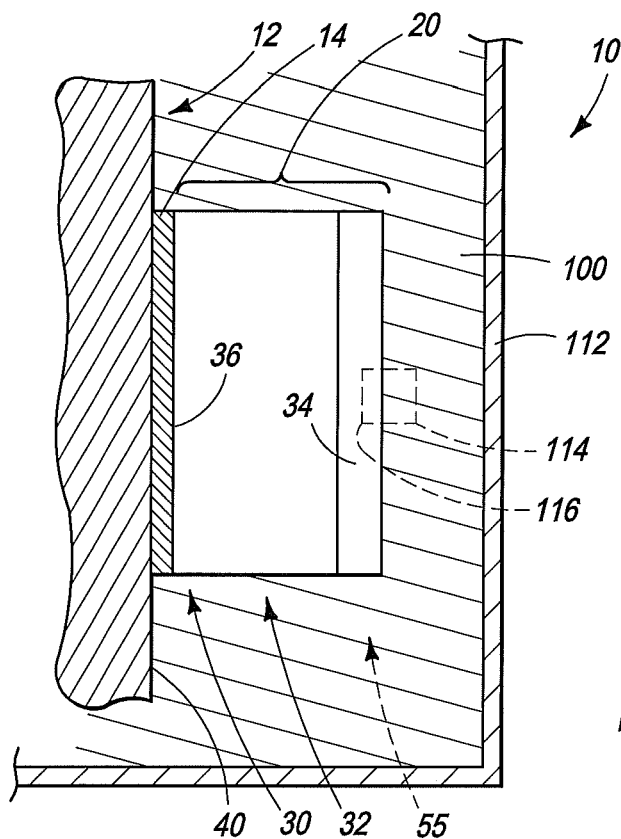
FIG. 10 is a schematic diagram showing a support assembly of an orthodontic appliance secured to a tooth while a mold is being made of the tooth and attached portion of the orthodontic appliance.

As discussed, the corrective assembly of an orthodontic appliance according to the present disclosure may be intentionally removed from the corresponding support assembly when it is necessary to produce a mold of the patient's teeth (and optionally the attached support assemblies). This is schematically illustrated in FIG. 10, in which a support assembly 20 is shown coupled to a patient's tooth 12. Also indicated in FIG. 10 is a molding compound 100 that is positioned in the patient's mouth to conform to the shape of the teeth (and attached support assemblies and/or other portion of appliances 10). In FIG. 10, the molding compound is shown being supported on a carrier, or tray, 112 that is inserted into the patient's mouth after being at least partially filled with uncured, or unset, molding compound. After the molding compound is sufficiently cured, or set, such as after the passage of time, the application of heat, the application of light, etc., the tray and molding compound are removed from the patient's mouth, nondeformably removing the mold from the patient's teeth and at least the support assemblies of any orthodontic assemblies attached thereto. By "nondeformingly," it is meant that the portion of the mold that corresponds to at least the portions of the patient's teeth to which the support assemblies are attached is not deformed, structurally altered, or otherwise damaged or permanently reshaped as the mold is removed from the patient's mouth.

As such, an exemplary method suitable for creating a mold of a patient's teeth to which are installed one or more orthodontic appliances each including a support assembly bonded to a tooth and a corresponding corrective assembly removably coupled to the support assembly (as discussed in greater detail above), includes removing a corresponding corrective assembly from a support assembly, applying unset molding compound to the patient's teeth (and to at least the support assemblies bonded to the teeth), setting the molding compound into a mold, and nondeformably removing the mold from the patient's teeth (and support assemblies).

Figure 11:
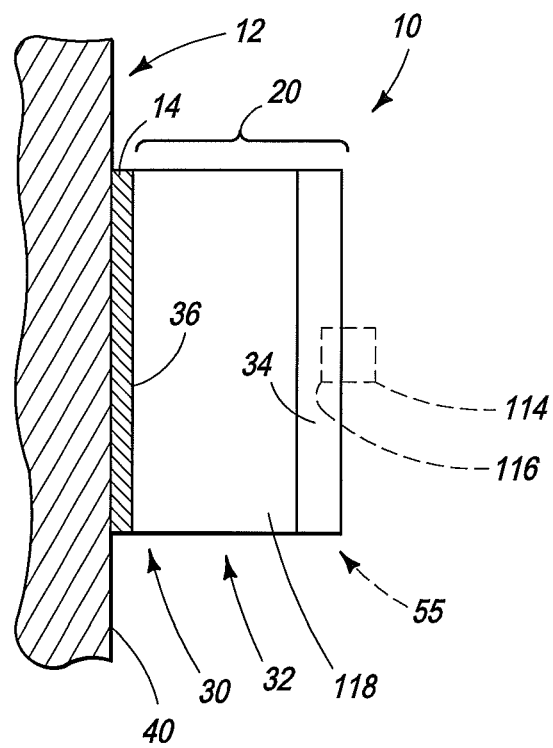
FIG. 11 is a schematic side elevation view of a support assembly of an orthodontic appliance that may be used with systems and methods according to the present disclosure, with the support assembly including a marker portion.

As discussed, in some applications it may be desirable to determine from the produced mold the position of the archwire-receiving slot of the assembled orthodontic appliance relative to the corresponding tooth. The mold-defined position of the support assembly may indicate this position or enable calculation of this position (as the dimensions of the corrective assembly, and/or the archwire are known). Thus, some exemplary methods may further include, subsequent to creating and nondeformably removing a mold, determining the position of the wire engaging portion of the removed corrective assembly from the mold. As discussed, it is also within the scope of the present disclosure that the support assembly includes an internally or externally projecting indicator, such as a tab, rib, indicia, or the like, that indicates on the support assembly the relative position of the archwire-receiving slot. Because the produced mold will include an impression of the support assembly, it will also include a representation (mold portion) that corresponds to the indicator. A support assembly with such an indicator is schematically illustrated in FIG. 11, with reference numeral 114 schematically indicating an example of an indicator that projects externally from, or away from, the support assembly, and reference numeral 116 schematically indicating an example of an indicator that projects internally into, or which is recessed in, the support assembly. Thus, some exemplary embodiments may further include, subsequent to creating and nondeformably removing a mold, determining the position of the wire engaging portion of the removed corrective assembly from the impression of the support assembly in the mold.

In some exemplary methods for creating a mold of a patient's teeth to which are installed one or more orthodontic appliances discussed in detail herein, an existing support assembly may be configured to indicate or otherwise represent the position of the archwire-receiving slot (or wire engaging portion) of the corresponding corrective assembly, for example by affixing an externally projecting indicator (such as indicator 114) to the support assembly, or by inscribing, etching, or otherwise including an internally projecting indicator (such as indicator 116) to the support assembly.

As also discussed, the orientation of a support assembly's perimeter may indicate or otherwise represent the position of the archwire-receiving slot (or wire engaging portion). For example, a support assembly defined by a perimeter surface may be configured to indicate, such as via the shape of the perimeter surface, the position of the archwire-receiving slot. FIG. 11 shows a support assembly with a perimeter surface 118, which may be shaped in such a manner. Such a support assembly may be provided with a shaped perimeter surface prior to installing the support assembly to a patient's tooth, or the perimeter surface of an installed support assembly may be shaped prior to the application of unset molding compound in order to create a mold.

As also discussed, in some embodiments, it may be desirable to replace the corrective assembly with a marker assembly prior to forming the mold, with the marker assembly defining an archwire-receiving slot (or other wire engaging portion) that corresponds to, or otherwise represents, the position and orientation of the corresponding slot (and/or portion) of the corrective assembly that was removed from the support assembly. FIG. 12 schematically indicates at 120 an illustrative, non-exclusive example of such a marker assembly mounted on a support assembly. The marker assembly includes a marker coupling portion 122 adapted to releasably engage corresponding structure of the support assembly (such as via engagement assembly 55), a body 124 extending from the marker coupling portion, and a marker portion 126 on the body adapted to indicate, when the marker assembly is coupled with the support assembly, the position of the wire engaging portion of the corresponding corrective assembly when coupled with the support assembly. Marker portion 126 of marker assembly 120 is shown as an archwire-receiving slot 128, and thus may structurally replicate the wire engaging portion of a corrective assembly, but may be any structure adapted to indicate the position of the wire engaging portion of the corrective assembly.

Also, as shown, body 124 of marker assembly 120 is defined by a perimeter surface, indicated at 130, that is free of projections extending in a direction generally parallel to the surface of the portion of the tooth to which the support assembly is bonded. As discussed above, such a perimeter surface may prevent removal of a marker assembly from a support assembly during nondeformable removal of the setup, or cured, mold, and/or may also prevent damage or other deformation of the mold when removed. However, the marker assembly may alternatively be designed to be removed from the support assembly as the setup, or cured, molding compound is removed from the patient's mouth, such as by the forces applied thereto as the molding compound is nondeformably removed. For example, as discussed above, the marker coupling portion 122 may be adapted to establish a desired bond strength with the support assembly relative to that established between the support assembly and a corrective assembly, to assist or prevent the marker assembly debonding from the support assembly upon nondeformable removal of a created mold.

As such, illustrative, non-exclusive methods of creating a mold may additionally include, prior to applying unset molding compound, coupling a marker assembly to the support assembly, the marker assembly including a marker portion configured to represent the wire engaging portion of the corresponding corrective assembly. Moreover, in some methods, nondeformably removing the mold may include contemporaneous removal of the marker assembly from the support assembly, or the marker assembly may be removed subsequent to and separately from nondeformably removing the marker assembly from the support assembly.

Moreover, some methods of creating a mold may additionally include, subsequent to nondeformably removing the mold, reattaching or coupling the corresponding corrective assembly to the support assembly, for example in order to resume orthodontic treatment.

It is believed that the disclosure set forth above encompasses multiple distinct inventions with independent utility. While each of these inventions has been disclosed in a preferred form or method, the specific alternatives, embodiments, and/or methods thereof as disclosed and illustrated herein are not to be considered in a limiting sense, as numerous variations are possible. The present disclosure includes all novel and non-obvious combinations and subcombinations of the various elements, features, functions, properties, methods and/or steps disclosed herein. Similarly, where any disclosure above or claim below recites "a" or "a first" element, step of a method, or the equivalent thereof, such disclosure or claim should be understood to include one or more such elements or steps, neither requiring nor excluding two or more such elements or steps.

Inventions embodied in various combinations and subcombinations of features, functions, elements, properties, steps and/or methods may be claimed through presentation of new claims in a related application. Such new claims, whether they are directed to a different invention or directed to the same invention, whether different, broader, narrower, or equal in scope to the original claims, are also regarded as included within the subject matter of the present disclosure.

The invention claimed is:

1. An orthodontic treatment method for a patient's teeth to which are installed orthodontic appliances that each include a support assembly bonded to a tooth and a corresponding corrective assembly with an archwire engaging portion removably coupled to the support assembly, the method comprising:

removing a plurality of corresponding corrective assemblies from a plurality of support assemblies that are operatively coupled to a corresponding plurality of teeth of the patient while leaving the plurality of support assemblies operatively coupled to the corresponding plurality of teeth of the patient;

coupling a marker assembly to at least one of the plurality of support assemblies, wherein the marker assembly includes a marker portion from which the position of the archwire engaging portion of the corresponding corrective assembly of the least one of the plurality of support assemblies may be determined;

forming, within the patient's mouth, a mold of the plurality of support assemblies and the patient's teeth to which the plurality of support assemblies are bonded, wherein the plurality of support assemblies includes the at least one of the plurality of support assemblies with the coupled marker assembly with the marker portion configured to represent the archwire engaging portion of the corresponding corrective assembly;

removing the mold from the patient's mouth without damaging or debonding the plurality of support assemblies or damaging or permanently deforming the mold; and determining, from the mold, the position of the archwire engaging portion of the removed corrective assembly of the at least one of the plurality of support assemblies to which the marker assembly was coupled.

2. The method of claim 1, wherein the method includes repeating the coupling to couple a plurality of marker portions to a corresponding number of the plurality of support assemblies, and further wherein the determining includes determining, from the mold, the position of the archwire engaging portions of the removed corrective assemblies of the support assemblies to which the marker assemblies were coupled.

3. The method of claim 1, wherein removing the mold contemporaneously removes the marker assembly from the at least one of the plurality of support assemblies.

4. The method of claim 1, further including creating, from the mold, an electronic representation of the patient's teeth.

5. The method of claim 1, further including creating, from the mold, a model of the patient's teeth and the orthodontic appliances bonded thereto.

6. The method of claim 5, wherein the model is a computer-generated model.

7. The method of claim 5, wherein the method further comprises using the model to determine future orthodontic treatment of the patient's teeth.

8. The method of claim 1, further comprising, subsequent to removing the mold, utilizing the mold to form an orthodontic device for use in orthodontic treatment of the patient's teeth.

9. The method of claim 8, wherein the orthodontic device includes an archwire.

10. The method of claim 8, wherein the orthodontic device includes a retainer.

11. The method of claim 10, wherein the orthodontic device includes a molded orthodontic treatment device.

12. The method of claim 1, wherein the determining the position of the archwire engaging portion of the removed corrective assembly includes determining the position of the archwire engaging portion of the removed corrective assembly from an impression of the marker portion in the mold.

13. The method of claim 1, wherein the determining the position of the archwire engaging portion of the removed corrective assembly includes determining the position of the archwire engaging portion of the removed corrective assembly based on the position of the marker portion in the mold.

14. The method of claim 13, wherein the determining the position includes determining the position of the archwire engaging portion of the removed corrective assembly by detecting at least one of the color, luminescence, or radiative property of the marker portion in the mold.

15. The method of claim 1, wherein the determining the position includes determining the position of the archwire engaging portion of the removed corrective assembly using at least one of a CT scanner and an RF scanner.

16. The method of claim 1, wherein the determining the position includes creating a model from the mold using a destructive process in which the mold is destroyed.

17. The method of claim 1, further comprising, subsequent to removing the mold, removing the marker assembly from the at least one of the plurality of support assemblies and recoupling the corresponding corrective assembly to the support assembly.

18. The method of claim 1, further comprising, subsequent to removing the mold, removing the marker assembly from the at least one of the plurality of support assemblies, selecting a corrective assembly to be coupled to the at least one of the plurality of support assemblies responsive at least in part to the mold or a model formed from the mold, and coupling the selected corrective assembly to the support assembly.

19. The method of claim 1, wherein the marker portion is configured to represent the archwire engaging portion of the corresponding corrective assembly.

20. The method of claim 1, wherein the marker portion includes an archwire engaging portion that conforms to the shape and position of the archwire engaging portion of the corresponding corrective assembly but is free from lateral projections extending in a direction generally parallel to the portion of the patient's tooth to which the at least one of the plurality of support assemblies is bonded.

21. The method of claim 1, wherein the marker portion structurally replicates the archwire engaging portion of the corresponding corrective assembly but is unsuitable for use as a corrective assembly during tooth-aligning use of the orthodontic appliance with an archwire.

22. An orthodontic treatment method for a patient's teeth to which are installed orthodontic appliances that each include a support assembly bonded to a tooth and a corresponding corrective assembly with an archwire engaging portion removably coupled to the support assembly, the method comprising:
  removing a plurality of corresponding corrective assemblies from a plurality of support assemblies that are operatively coupled to a corresponding plurality of teeth of the patient while leaving the plurality of support assemblies operatively coupled to the corresponding plurality of teeth of the patient, wherein the at least one of the plurality of support assemblies from which the corresponding corrective assembly was removed includes a marker portion configured to represent the archwire engaging portion of the corresponding corrective assembly;
  forming, within the patient's mouth, a mold of the plurality of support assemblies and the patient's teeth to which the plurality of support assemblies are bonded, wherein the plurality of support assemblies includes the at least one of the plurality of support assemblies that includes a marker portion configured to represent the archwire engaging portion of the corresponding corrective assembly;
  removing the mold from the patient's mouth without damaging or debonding the plurality of support assemblies or damaging or permanently deforming the mold; and
  determining, from the mold, the position of the archwire engaging portion of the removed corrective assembly of the at least one of the plurality of support assemblies to which the marker assembly was coupled.

23. The method of claim 22, further including creating, from the mold, an electronic representation of the patient's teeth.

24. The method of claim 22, further including creating, from the mold, a model of the patient's teeth and the orthodontic appliances bonded thereto.

25. The method of claim 24, wherein the model is a computer-generated model.

26. The method of claim 24, wherein the method further comprises using the model to determine future orthodontic treatment of the patient's teeth.

27. The method of claim 22, further including using the mold to configure an archwire for use in orthodontic treatment of the patient's teeth.

28. The method of claim 22, further comprising, subsequent to removing the mold, utilizing the mold to form an orthodontic device for use in orthodontic treatment of the patient's teeth.

* * * * *

UNITED STATES PATENT AND TRADEMARK OFFICE
CERTIFICATE OF CORRECTION

| | | |
|---|---|---|
| PATENT NO. | : 8,070,488 B2 | |
| APPLICATION NO. | : 12/852885 | |
| DATED | : December 6, 2011 | |
| INVENTOR(S) | : Christopher C. Cosse | |

It is certified that error appears in the above-identified patent and that said Letters Patent is hereby corrected as shown below:

Column 14, Line 21, after "assembly of the" please insert --at--.

Signed and Sealed this
Twentieth Day of March, 2012

David J. Kappos
*Director of the United States Patent and Trademark Office*